(12) United States Patent
Haverkost et al.

(10) Patent No.: US 12,156,980 B2
(45) Date of Patent: Dec. 3, 2024

(54) DEVICES, SYSTEMS, AND METHODS FOR A CATHETER ACCESSORY

(71) Applicant: Boston Scientific Scimed, Inc., Maple Grove, MN (US)

(72) Inventors: Patrick A. Haverkost, Corcoran, MN (US); Joel N. Groff, Delano, MN (US); Joel M. WasDyke, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 734 days.

(21) Appl. No.: 17/001,959

(22) Filed: Aug. 25, 2020

(65) Prior Publication Data

US 2021/0060303 A1 Mar. 4, 2021

Related U.S. Application Data

(60) Provisional application No. 62/891,720, filed on Aug. 26, 2019.

(51) Int. Cl.
*A61M 25/04* (2006.01)
*A61B 17/12* (2006.01)
(Continued)

(52) U.S. Cl.
CPC ....... *A61M 25/04* (2013.01); *A61B 17/12136* (2013.01); *A61M 25/0054* (2013.01);
(Continued)

(58) Field of Classification Search
CPC ...... A61M 25/0102; A61M 2025/1056; A61M 25/04; A61M 25/0054; A61M 25/09041;
(Continued)

(56) References Cited

U.S. PATENT DOCUMENTS

| 5,882,334 A | 3/1999 | Sepetka et al. |
| 8,251,948 B2 | 8/2012 | Goldman |

(Continued)

OTHER PUBLICATIONS

International Search Report and Written Opinion for the International Patent Application No. PCT/US2020/047744, mailed Dec. 15, 2020, 21 pages.

(Continued)

*Primary Examiner* — Michael J Tsai
*Assistant Examiner* — Rachel T. Smith
(74) *Attorney, Agent, or Firm* — Seager, Tufte & Wickhem, LLP

(57) ABSTRACT

The present disclosure, in its various aspects, is directed generally to medical devices, and more specifically to catheter accessory devices and related systems and methods. In an embodiment, an instrument accessory device may include a body with an instrument lumen through which an instrument may extend through. An expandable member may be disposed about the distal end of the body. An elongate delivery member may be attached to the body and in communication with the expandable member at a distal end of the delivery member. The delivery member may be configured to slide the instrument lumen of the body and the expandable member along the length of the instrument when extended therethrough. Other embodiments are addressed within.

16 Claims, 7 Drawing Sheets

(51) Int. Cl.
*A61M 25/00* (2006.01)
*A61M 25/01* (2006.01)
*A61M 25/09* (2006.01)
*A61M 25/10* (2013.01)

(52) U.S. Cl.
CPC .. *A61M 25/0102* (2013.01); *A61M 25/09041* (2013.01); *A61M 25/10184* (2013.11); *A61M 2205/0266* (2013.01)

(58) Field of Classification Search
CPC .... A61M 25/10184; A61M 2205/0266; A61B 17/12136; A61B 17/12031; A61B 17/1204; A61B 17/12045; A61B 17/12186
See application file for complete search history.

(56) References Cited

U.S. PATENT DOCUMENTS

| | | | |
|---|---|---|---|
| 10,130,762 | B2 | 11/2018 | Allen |
| 10,188,396 | B2 | 1/2019 | Folk et al. |
| 2002/0133081 | A1* | 9/2002 | Ackerman ............. A61B 5/085 600/593 |
| 2004/0116848 | A1 | 6/2004 | Gardeski et al. |
| 2008/0243171 | A1 | 10/2008 | Ressemann et al. |
| 2010/0152613 | A1* | 6/2010 | Ryan ..................... A61M 25/00 600/566 |
| 2016/0051799 | A1* | 2/2016 | Daniels .............. A61M 25/1011 604/103.11 |
| 2019/0111234 | A1 | 4/2019 | Jaroch et al. |
| 2021/0147462 | A1* | 5/2021 | Wells ................ A61M 25/1011 |

OTHER PUBLICATIONS

TriSalus Life Science—TheSurface Infusion Systems—retrieved Mar. 12, 2021—URL: https://web.archive.org/web/20191221054043/https://surefireinfusion.com/.

Cision—PRWeb ""Surefire Medical Launches Next Generation Infusion System ST-LT and Specialty Catheters at SIR—Maximizing Targeted Delivery of Embolics Without Reflux"" Apr. 13, 2013—URL: https://www.prweb.com/releases/2013/4/prweb10628816.htm.

* cited by examiner

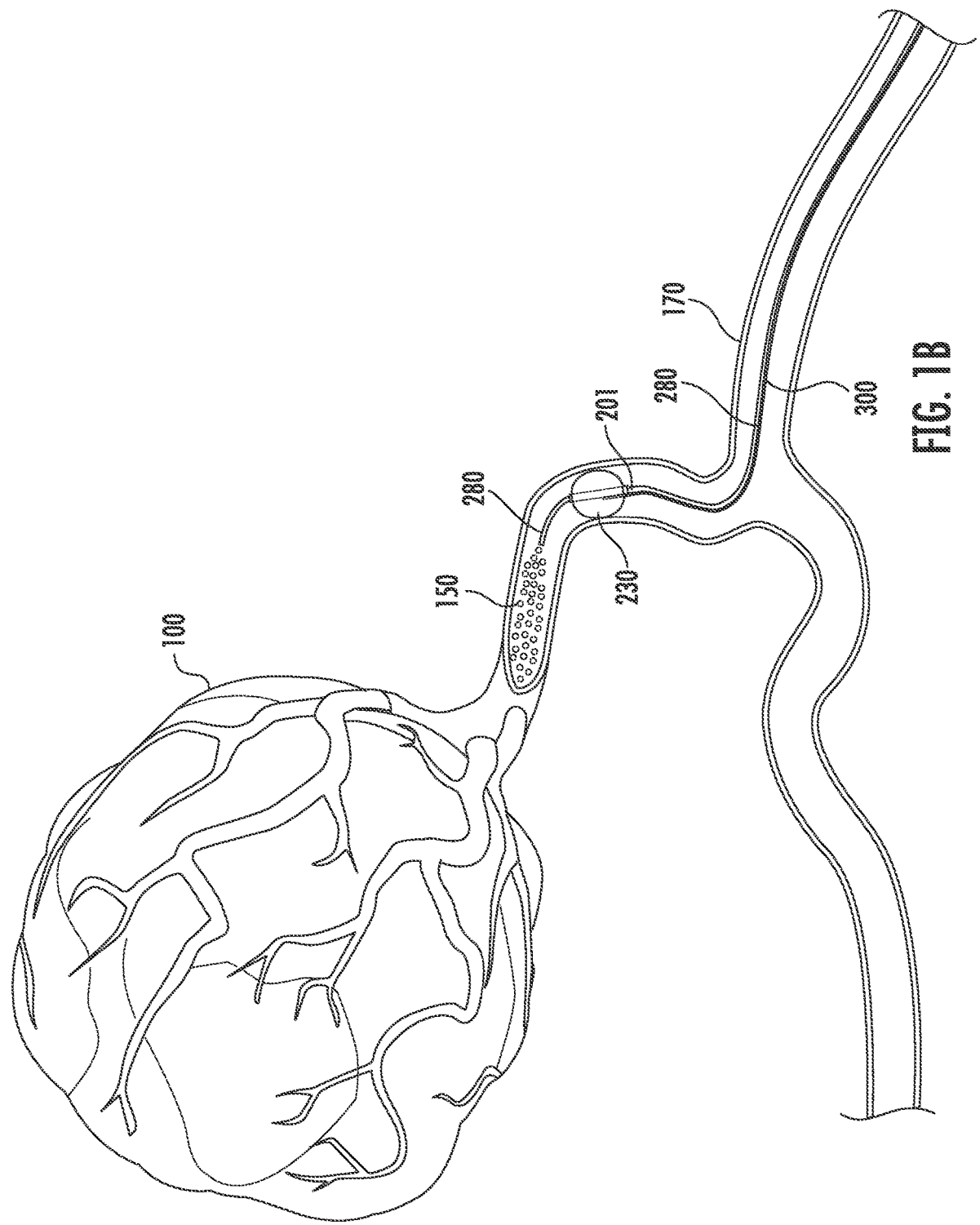

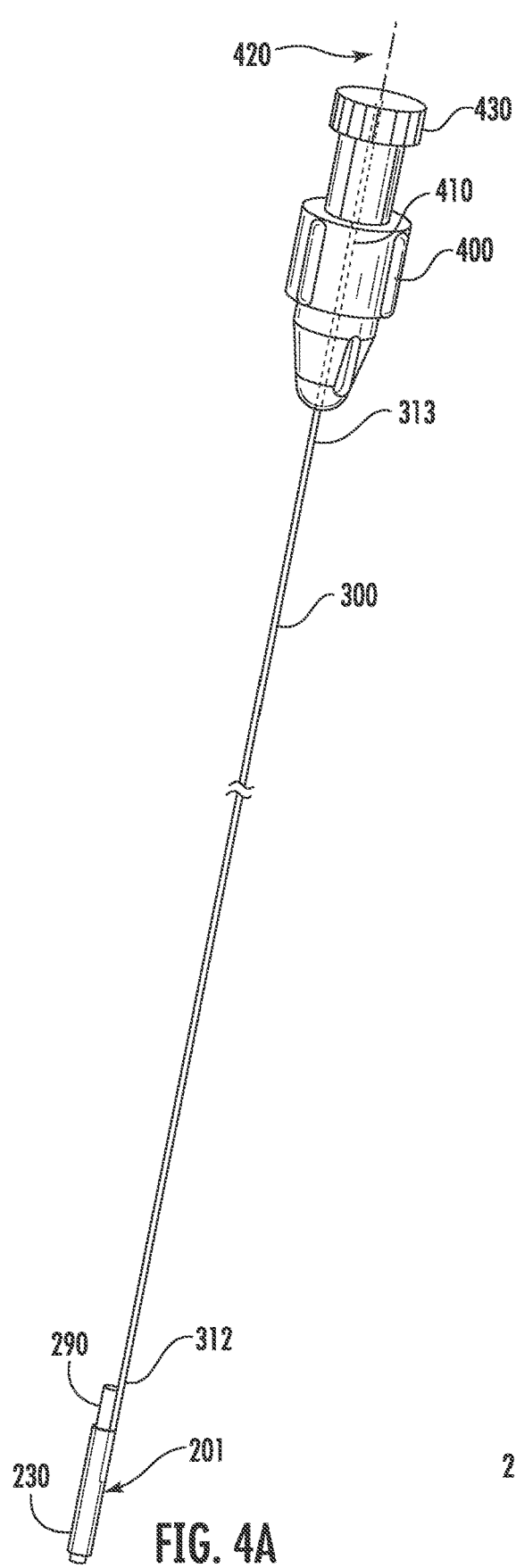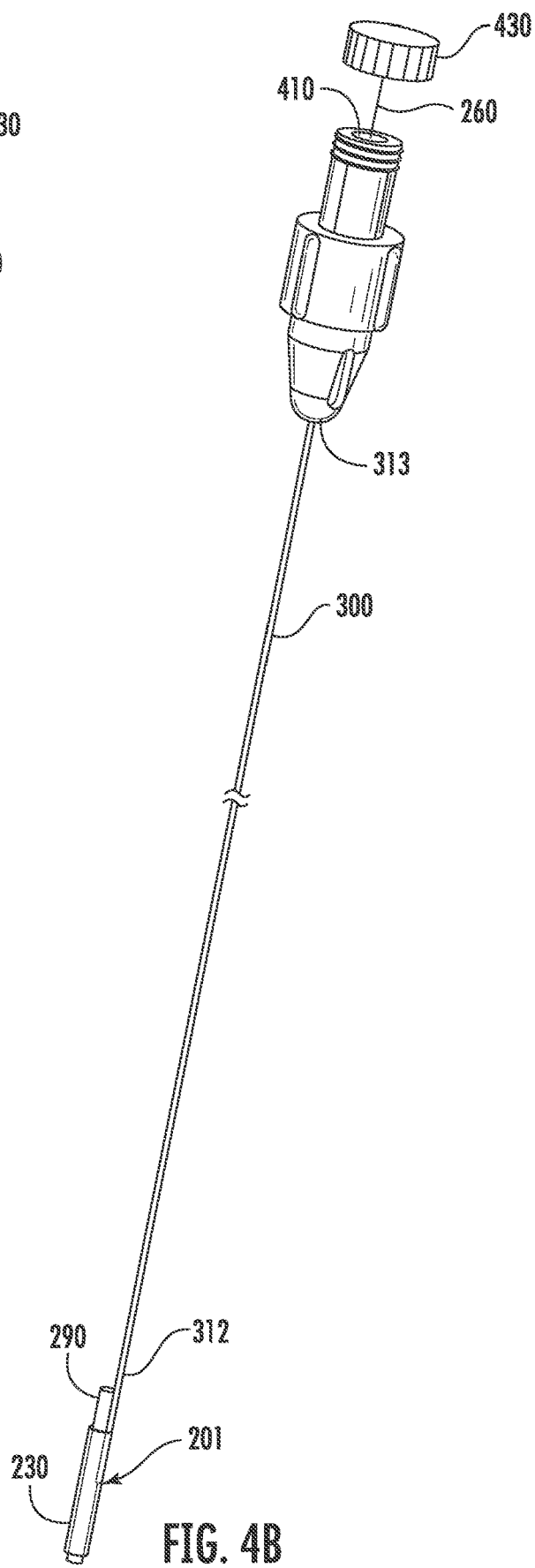

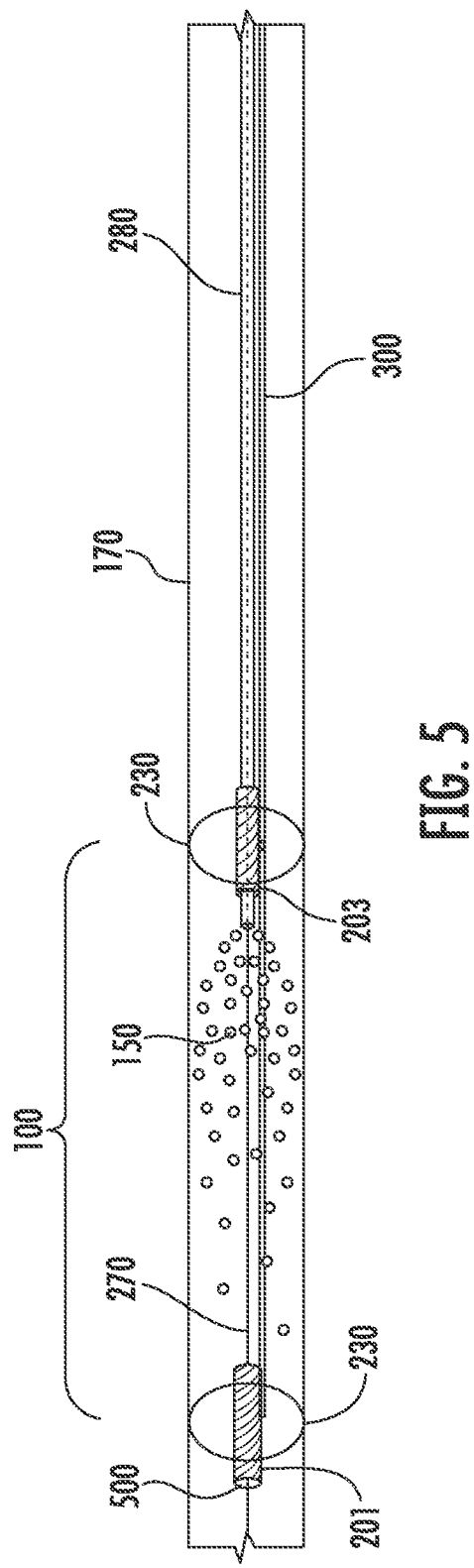

DEVICES, SYSTEMS, AND METHODS FOR A CATHETER ACCESSORY

PRIORITY

This application claims the benefit of priority under 35 USC § 119 to United States Provisional Patent Application Ser. No. 62/891,720, filed Aug. 26, 2019 and titled "Devices, Systems, and Methods for a Catheter Accessory," the disclosures of which are incorporated by reference herein in their entirety and for all purposes.

FIELD

The present disclosure pertains to medical devices. More particularly, the present disclosure pertains to catheter accessory devices and related systems and methods.

BACKGROUND

Catheters are used in procedures treating conditions within the body, e.g., by delivering fluid to a treatment site. It may be desirable to deliver a fluid to the treatment site, but not to other sites within the body. For example, a catheter may be used to navigate to a site within a vessel in order to provide treatment. An embolic material could be used as the treatment fluid. Undesired migration of the embolic (e.g., reflux) could occur proximally around the outside of the catheter, possibly migrating proximally beyond an intended treatment site.

It is with the above considerations in mind that the improvements of the present disclosure may be useful.

SUMMARY

The present disclosure, in its various aspects, is directed generally to medical devices, and more specifically to catheter accessory devices, implementation methods, and related delivery systems. Embodiments according to the present disclosure, including as described herein, may increase effectiveness and efficiency regarding the treatment of conditions within the body, e.g., treatment of tumors with embolic materials. Disclosed herein are medical devices such as instrument accessories and catheter systems that may deliver targeted treatment to a treatment site.

In an aspect, an instrument accessory device may include a body having a proximal end, a distal end, a longitudinal axis, and a wall defining an instrument lumen extending between the proximal end and the distal end along the longitudinal axis of the body. The instrument lumen may have an inlet and an outlet at the respective proximal end and distal end of the body. The instrument lumen may be configured to slidingly receive a length of an instrument extendible therethrough. An expandable member may be disposed about the wall at the distal end of the body. The expandable member may extend between a proximal end and a distal end along a longitudinal axis of the expandable member. The expandable member may be disposed about the wall of the body. The expandable member may be adhered to the wall at the proximal and distal ends of the expandable member. An elongate delivery member may be attached to the body, and may be in communication with the expandable member at a distal end of the delivery member. The delivery member may be configured to slide the instrument lumen of the body and the expandable member along the length of the instrument when extended therethrough.

In various embodiments, the expandable member may be disposed about the wall of the body, and may be adhered to the wall at the proximal and distal ends of the expandable member. In various embodiments described here or otherwise, an inflation lumen may extend between a proximal end and the distal end of the elongate delivery member, and the inflation lumen may be in fluid communication with the expandable member elongate delivery member. The distal end of the elongate delivery member may be disposed between the proximal end of the expandable member and the distal end of the expandable member. The instrument may be a guidewire, a catheter, or the catheter combined with the guidewire. The expandable member may be pneumatically, electrically, or mechanically expandable. The expandable member may comprise a self-expanding or shape memory material. The inflation lumen may be configured to receive a stylet. The inflation lumen may be configured to communicate a fluid between the proximal end of the elongate delivery member and the expandable member. A handle may be disposed at the proximal end of the elongate delivery member. The inflation lumen may be continuous with a handle lumen extending along a longitudinal axis of the handle. The stylet may have a cap at a proximal end of the stylet. The cap may be reversibly coupled to the handle. The distal end of the elongate delivery member and the proximal end of the expandable member may be adhered to the wall at the proximal end of the body. The expandable member may comprise a compliant or semi-compliant balloon. The distal end of the elongate delivery member may be flowed with the expandable member.

In an aspect, a catheter system may include an instrument. The system may include a catheter accessory slidably disposed about the catheter. The catheter accessory may comprise a body having a proximal end, a distal end, a longitudinal axis, and a wall defining an instrument lumen extending between the proximal and distal end along the longitudinal axis of the body, thereby defining an instrument lumen an inlet and an outlet at the respective proximal end and distal end of the body, the instrument lumen configured to slidingly receive a length of an instrument extendible therethrough. The catheter accessory may also comprise an expandable balloon coupled to the body. The catheter accessory may comprise an elongate delivery member attached at a distal end to the body and having an inflation lumen extending therethrough in fluid communication with the expandable balloon.

In various embodiments, the catheter system may further comprise a stylet, the stylet removably receivable within the elongate delivery member. The catheter system may further comprise a catheter disposable about the guidewire. The expandable balloon of the system may comprise a compliant or semi-compliant balloon.

In an aspect, a method of delivering treatment fluid within a patient may comprise inserting a guidewire through an instrument lumen of a first catheter accessory, the accessory including a distal expandable member. The guidewire may be advanced through a body lumen to a first treatment site within a patient. A catheter may be inserted into the instrument lumen about the guidewire. The catheter may be advanced along the catheter proximal to the first treatment site. The first catheter accessory may be advanced along the catheter to a position proximal to the first treatment site. The expandable member may be expanded about the first catheter accessory to occlude the body lumen at the proximal position. A treatment fluid may be supplied through the first catheter to the first treatment site.

In various embodiments described here or otherwise, the catheter accessory may include an inflation lumen attached to the expandable member and expanding may comprise supplying a fluid through the inflation lumen to inflate the expandable member. The expandable member may be a compliant or semi-compliant balloon. The treatment fluid may comprise an embolic material. The method may further comprise a stylet reversibly coupled to the inflation lumen, the stylet may be configured to stiffen the inflation lumen during the advancing of the first catheter accessory. A method may further include deflating the expandable member, moving the catheter to a second treatment site, moving the first catheter accessory to a position proximal to the second treatment site, re-inflating the expandable member, and supplying the treatment fluid through the catheter to the second treatment site. A method may include prior to moving the first catheter accessory along the catheter to the first treatment site, disposing a stylet within the inflation lumen. The method may further include inserting the guidewire and catheter into an access sheath. The treatment site may be a tumor. A method may further include inserting the guidewire through a second instrument lumen of a second catheter accessory with a second inflation lumen. The second catheter accessory may include a second distal expandable member. The second expandable member may be expanded about the accessory to occlude the body lumen at the proximal position. The first treatment site may be located between the first expandable member and the second expandable member. A method may further include a first expandable member occluding a different body lumen than a second expandable member. A method may include a first and second catheter accessory with a single inflation lumen in fluid communication with an expandable member of each of the first and second catheter accessory.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIG. 1B illustrates a partial cross-sectional view of a catheter system with an instrument accessory device within a body and an exemplary catheter, such as the catheter of FIG. 1A, extended therethrough, in accordance with an embodiment of the present disclosure.

FIG. 4A illustrates a perspective view of the instrument accessory device of FIGS. 2 and 3 including a proximal end with a handle and stylet, in accordance with an embodiment of the present disclosure.

FIG. 4B illustrates a perspective view of the instrument accessory device of FIG. 4A with the stylet partially removed.

FIG. 5 illustrates a partial cross-sectional view of two instrument accessory devices within a body, in accordance with an embodiment of the present disclosure.

Figure 1A:
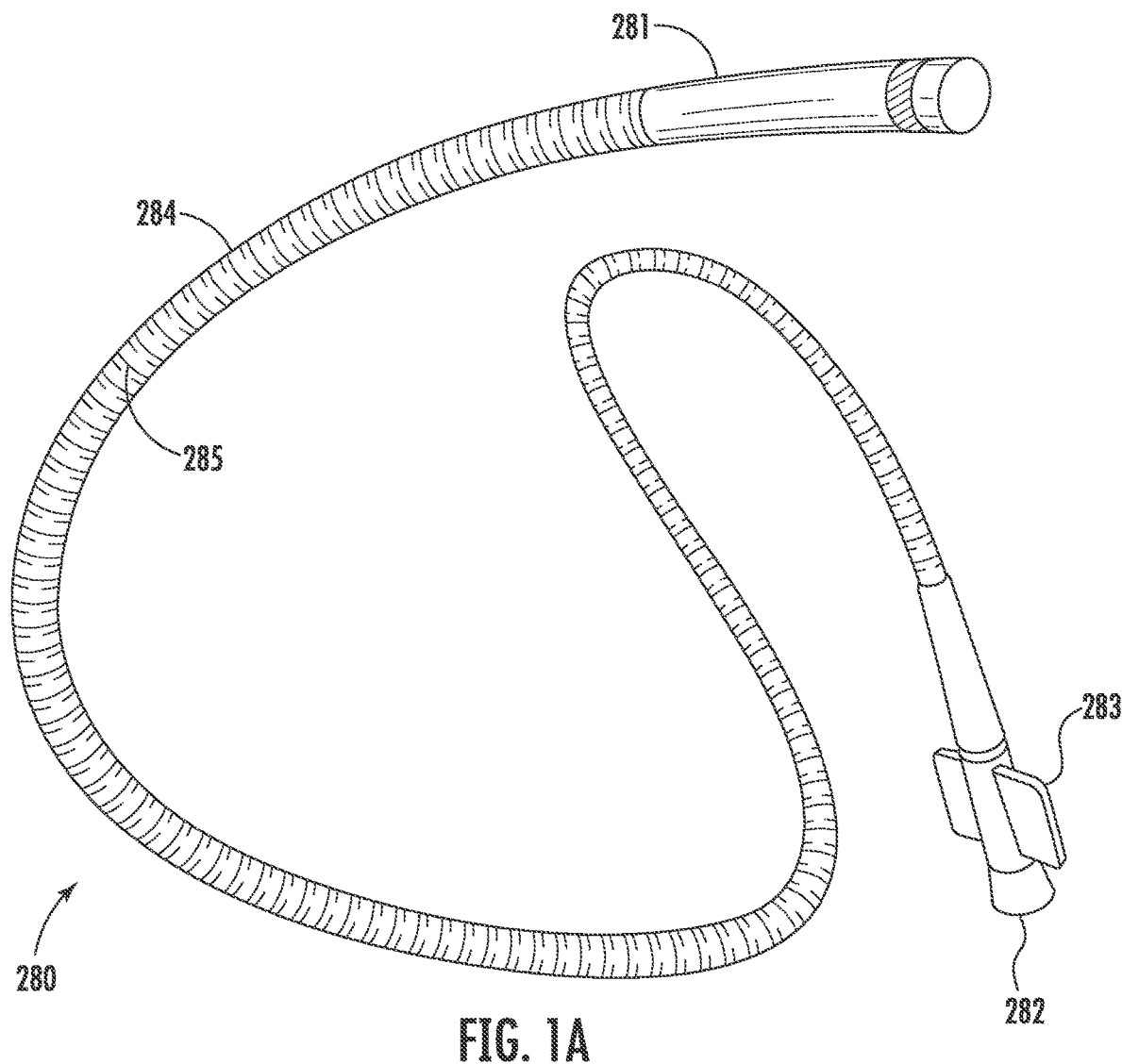
FIG. 1A illustrates an exemplary catheter of a type described as an embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Various embodiments according to the present disclosure are described below. As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The detailed description should be read with reference to the drawings, which are not necessarily to scale, depict illustrative embodiments and are not intended to limit the scope of the invention.

Embodiments of the present disclosure may include an instrument accessory, as a device for use with an instrument. An instrument may be a catheter, a guidewire, or a combination of a catheter with a guidewire (e.g., catheter pre-loaded onto a catheter), or the like. A catheter may be a micro-catheter. The device may include various components and configurations. Embodiments of this disclosure may comprise a catheter system. A catheter system may include a catheter, a guidewire, a handle, a catheter accessory, an access sheath, a stylet, a treatment fluid, and/or an inflation fluid, or the like. Embodiments of the devices and systems may be used to occlude the space around the instrument, during delivery of a treatment fluid, in order to prevent undesired movement of the fluid (e.g., reflux of fluid proximally along the outside of the instrument) at a treatment site. Various embodiments described herein comprise a device having an expandable member about an instrument lumen that can slidingly receive an instrument extended therethrough. The device and/or instrument may be extended relative to the other to place the expandable member of the device at a desired position in a body lumen relative to a treatment site. The expandable member once expanded within the body lumen may substantially prevent or prevent a treatment fluid from passing beyond the expandable member. In some embodiments, the treatment fluid may be a diagnostic fluid. In some embodiments, the body lumen may include a lumen, organ, vessel, passage, or the like, within, e.g., the cardiovascular or peripheral vascular system, the respiratory system, circulatory system, digestive system, urinary and/or reproductive systems, or the like.

A number of medical procedures, including surgery, chemotherapy, radiation therapy, embolization therapy (with or without a drug or radiation component), can be used for the treatment of cancer or other conditions in the body. Radiation therapy is therapy using ionizing radiation, and can be performed externally or internally. A form of internal radiation therapy called radioembolization specifically targets treatment sites with radioactive microspheres. This type of treatment may be used, e.g., for patients with surgically unresectable cancers, e.g., in the liver.

For various uses of catheters or other instruments, within the various body lumens and for the various purposes, described above, the embodiments of the accessory devices, systems and methods of the present disclosure may be utilized to enable the physician to perform procedures with greater precision, accuracy, and ease than without the accessory devices.

An instrument accessory device may include an expandable member. An expandable member may be a balloon, a mesh, a braid, a flap, or the like, and may be mechanically actuated, electrically actuated, pneumatically actuated, inflated, or the like. An expandable member may transition from an unexpanded configuration to an expanded configuration to occlude, stretch, establish patency, or maintain patency of a body lumen.

An accessory device may include an elongate delivery member. A proximal end of the elongate delivery member may be manipulated to move the accessory device within a patient. The elongate delivery member may have a lumen that may be in fluid communication with an expandable member. The lumen may accept an inflation fluid for expanding and un-expanding the expandable member. The lumen may accept a stylet for manipulation of the elongate delivery member.

One method of delivering treatment fluid, e.g., radioembolization, is by use of a catheter. A distal end of the catheter may be delivered to or proximal to a treatment site over a guidewire. Treatment fluid, e.g., radioactive microspheres, may be delivered to the treatment site through the catheter via a proximal end of the catheter that remains outside of the body. A potential concern with this method of treatment may be that the radioactive microspheres move through the body lumen, e.g., through an artery with the flow of blood, rather than remaining at the treatment site.

Referring to FIG. 1A, an embodiment of a catheter of the type described in the present disclosure is illustrated. The catheter 280 is one example of an instrument that can be used with an instrument accessory device described further herein. The catheter 280 comprises a distal end 281 and a proximal end 282 with a lumen therethrough. A handle 283 at the proximal end 282 may be operated by a medical professional to manipulate the catheter 280. The catheter 280 may include cuts or channels 285 along a wall 284 of the catheter 280 in order to facilitate movement and flexibility within a patient, e.g., by operation of the handle 283.

Referring to FIG. 1B, a view of a catheter system within the body is illustrated according to an embodiment of the present disclosure, which includes an instrument accessory device 201 slidably disposed at an end of a catheter 280 (e.g., the catheter 280 of FIG. 1A). A treatment fluid 150 is supplied through the catheter 280 and distally towards a treatment site 100. An expandable member 230 (e.g., compliant balloon) of the device 201 substantially occludes a body lumen 170 while in the expanded configuration. The expandable member 230 may be transitioned from an unexpanded configuration to an expanded configuration by supply of an inflation fluid through an inflation lumen of an elongate delivery member 300. The body lumen 170, e.g., blood vessel, is substantially occluded in a direction proximal to the expandable member and a distal end of the catheter 280, allowing the treatment fluid 150 to flow substantially towards the treatment site 100, rather than proximally through the body lumen 170.

Figure 2A:
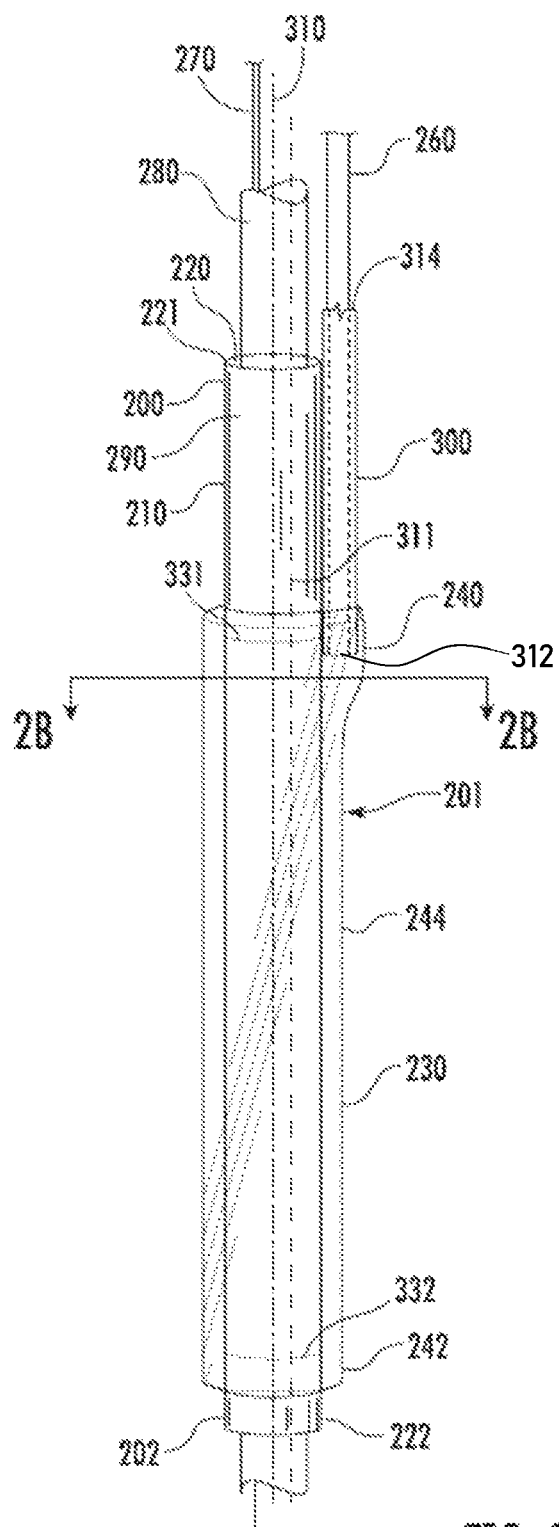
FIG. 2A illustrates a perspective view of an instrument accessory device in an unexpanded configuration, in accordance with an embodiment of the present disclosure.
Figure 2B:
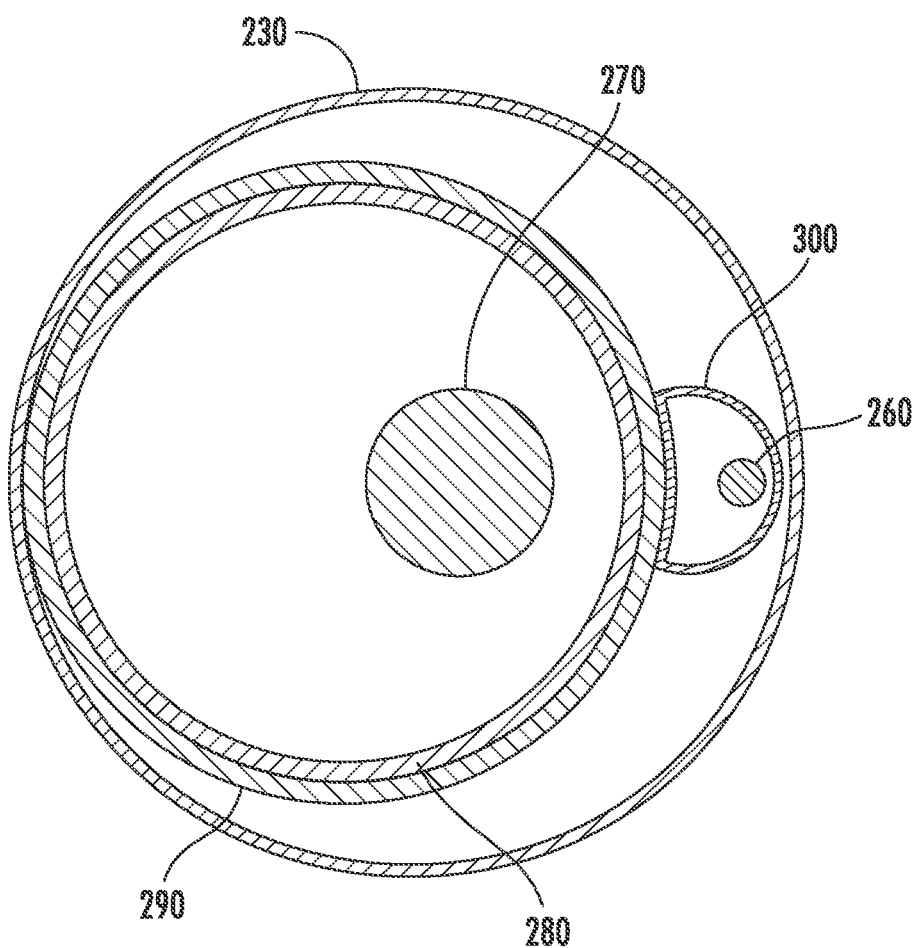
FIG. 2B illustrates a cross-sectional view of the instrument accessory device of FIG. 2A.
Figure 3:
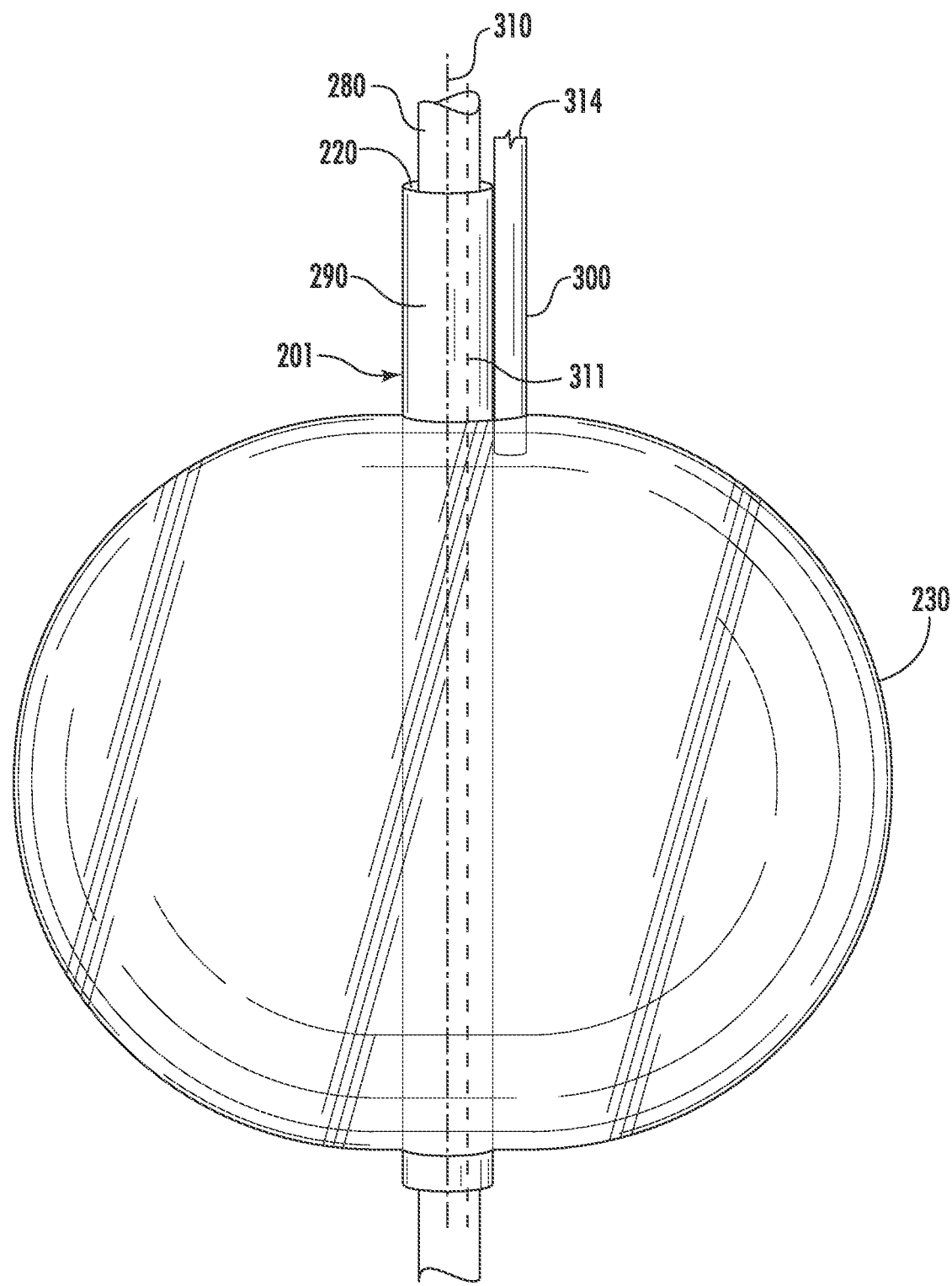
FIG. 3 illustrates a perspective view of the instrument accessory device of FIGS. 2A and 2B in an expanded configuration.

Referring to FIGS. 2A, 2B, and 3, an instrument accessory device 201 is illustrated as part of a catheter system according to an embodiment of the present disclosure. The instrument accessory device 201 includes a body 290 having a proximal end 200, a distal end 202, and a longitudinal axis 310. A wall 210 of the body 290 extends between the proximal 200 and distal 202 ends along the longitudinal axis 310. The wall 210 defines an instrument lumen 220 having an inlet 221 at the proximal end 200, an outlet 222 at the distal end 202, and extending along the longitudinal axis 310. The instrument lumen 220 is configured to receive an instrument, e.g., a catheter 280 and/or a guidewire 270, that extends through the instrument lumen 220. An expandable member 230 having a proximal end 240 and a distal end 242 is illustrated in an unexpanded configuration in FIG. 2A. A wall 244 of the expandable member 230 extends between the proximal 240 and distal 242 ends along a longitudinal axis 311. The longitudinal axis of the body and the longitudinal axis of the expandable member may be parallel to each other, as shown, or may be offset from each other. The body and the expandable member may have a center axis as the longitudinal axis that may be coextensive or radially offset from each other. The expandable member 230 is disposed about the wall 210 at the distal end 202 of the body 290. The accessory device of FIGS. 2A, 2B, and 3, includes an elongate delivery member 300 having a proximal end (not shown), a distal end 312, and an inflation lumen 314 therethrough. The distal end 312 of the elongate delivery member 300 is between the proximal end 240 of the expandable member 230 and the distal end 242 of the expandable member 230 such that the inflation lumen 314 is in fluid communication with the expandable member 230. The proximal end 240 of the expandable member 230 is adhered to the body 290 and the elongate delivery member 300 at a proximal adhesion band 331. The distal end 242 of the expandable member 230 is adhered to the body 290 at the distal adhesion band 332. An adhesion band may be a location where the body, the expandable member, and/or an elongate delivery member are adhered to each other. The adhesion may be an adhesive, a tape, flowed material, welding (e.g., laser, ultrasonic, hot jaw thermal, etc.), melt/re-melt flow processes, or the like. The adhesion bands 331, 332 create a substantially tight fluid seal between an interior of the expandable member 230 and an exterior of the expandable member 230 such that an inflation fluid may be supplied through the inflation lumen 314 to transition the expandable member between the unexpanded configuration of FIG. 2A and an expanded configuration of FIG. 3. FIG. 3 illustrates the catheter system of FIG. 2A with the instrument accessory 210 in an expanded configuration. The expandable member 230 in the expanded configuration is illustrated in an ellipsoidal shape, but the expandable member 230 may be other shapes such as, e.g., a sphere, a torus, a combination thereof, or the like. When in the expanded configuration of FIG. 3, an inflation fluid is disposed through the elongate member 300. A catheter 280 extending through the instrument lumen 220 of the body 290 may be used to deliver a treatment fluid. With the expandable member 230 in the expanded configuration in a body lumen, the treatment fluid may be delivered distally out of the catheter 280 to the body lumen, and the treatment fluid may be substantially occluded from flowing proximally past the expandable member 230 along the longitudinal axis 310.

The catheter system is illustrated in a delivery configuration in FIGS. 2A and 2B such that the instrument accessory device 201 may be translated through the body 290 toward or away from a treatment site. The instrument lumen 220 is shown with a catheter 280 loaded over a guidewire 270 extending through the instrument lumen 220. The inflation lumen 314 is shown with a stylet 260 extending therethrough, which may be used to stiffen the inflation lumen of the delivery member during movement of the accessory device along an instrument. The stylet 260 may be coupled to the proximal end (not shown) of the elongate delivery member 300, such that the stylet 260 and member may be distally or proximally translated to distally or proximally translate the instrument accessory device 201 over the instruments (i.e., the catheter 280 and the guidewire 270).

Referring to FIGS. 4A and 4B, perspective views of the instrument accessory device 201 of FIGS. 2A-3 is illustrated in an unexpanded configuration. The portion of the instrument accessory device 201 depicted in FIGS. 2A-3 is shown at the distal end 312 of the elongate delivery member 300, including the body 290 and expandable member 230. A handle 400 is disposed at the proximal end 313 of the elongate delivery member 300. The inflation lumen is in fluid communication with a handle lumen 410 along a longitudinal axis 420 of the handle 400. A cap 430 is reversibly attached to the proximal end of the handle 400. The cap 430 may be reversibly coupled to the handle 400 by various means, e.g., threading, a snap-fit, a keyed notch, adhesive, or the like. A proximal end of the stylet 260 is attached to the cap 430 such that when the handle 400 coupled to the cap 430 is proximally or distally translated, the elongate delivery member 300, body 290, and expandable member 230 are likewise proximally or distally translated over an instrument disposed within the instrument lumen. The cap 430 may be removed from the handle 400, as illustrated in FIG. 4B, which proximally extracts the stylet 260 from the elongate delivery member 300. With the stylet 260 removed from the elongate delivery member, an inflation fluid may be supplied through the handle lumen 410, through the inflation lumen 314, and into the expandable member 230 such that the expandable member 230 transitions into the expandable configuration of FIG. 3.

With reference to FIG. 5, a partial cross-sectional view of two instrument accessory devices are illustrated within a body lumen 170 according to an embodiment of the present disclosure. A distal instrument accessory device 201 and a proximal instrument accessory device 203 may each have a body with an instrument lumen disposed about an instrument, e.g. a guidewire 270 and/or a catheter 280. The distal instrument accessory device 201 may have an instrument lumen which may only receive a guidewire 270. The distal instrument accessory device 201 and proximal instrument accessory device 203 may have one elongate delivery member 300 with an aperture for each of the expandable members 230, e.g., an aperture through a wall of the elongate delivery member 300 in fluid communication with the expandable member 230 of the proximal instrument accessory device 203. Alternatively, each device 201, 203 may include their own elongate delivery member 300. A distal cap 500 may be included on the distal instrument accessory device 201 that may have an aperture wide enough for a guidewire 270 to sealingly extend through such that the treatment fluid 150 may not flow distally past the distal cap 500. A treatment site 100 of the body lumen 170 to receive a treatment fluid 150 is between the devices 201, 203. This treatment site 100 has a longitudinal length between the devices 201, 203 that may be customized by translating one or both of the devices 201, 203 proximally and/or distally, e.g., to match a diseased area of the body lumen 170. The guidewire 270 may be moved such that it passes through the treatment site 100. The distal instrument accessory device 201 may be guided with a first stylet through the elongate delivery member 300 toward a distal end of the guidewire 270 distal to the treatment site and the proximal instrument accessory device 203 may be guided with a second stylet and/or the first stylet to a position proximal to the distal instrument accessory device 201 and proximal to the treatment site. The accessory device 201 may be further repositioned along the instrument to relocate the accessory device 201 with respect to a treatment site and/or the instrument. The first and/or second stylet(s) may be removed, and inflation fluid 150 may be supplied into the elongate delivery member(s) 300 of the distal and proximal instrument accessory devices 201, 203 to inflate the expandable members 230 on either side of the treatment site. A catheter may be passed over the guidewire and through the instrument lumen of the proximal accessory device to a position between the expandable members. Treatment fluid delivered through the catheter may be contained between the expandable members. Although both accessory devices 201, 203 are illustrated in the same body lumen 170, one accessory device 201, 203 may be located within a second body lumen, e.g., to substantially occlude the second body lumen with an expandable member 230.

In various embodiments, an alternative catheter 280 may extend through an instrument lumen of each of the proximal accessory device 203 and the distal accessory device 201. The catheter 280 may include a distal valve that may accommodate the guidewire 270 extended therethrough. The distal valve may seal tightly around the guidewire 270 such that the treatment fluid 150 may not flow distally past the distal valve. The catheter 280 may have one or more side apertures through a wall along the length of the catheter 280. The apertures may be positioned between the distal and proximal accessory devices 201, 203 within the treatment site 100. The treatment fluid 150 may be delivered through the catheter 280 and expelled through the apertures within the treatment site 100.

In various embodiments, a distal instrument accessory device 201 may be guided with a first stylet extended through a first elongate delivery member coupled to an expandable member 230 of the distal instrument accessory device 201 along a guidewire 270, thereby defining an adjustable distal end of a treatment site 100. A proximal instrument accessory device 203 may be guided with a second stylet extended through a second elongate delivery member coupled to an expandable member 230 of the proximal instrument accessory device 203 along the guidewire 270, thereby defining an adjustable proximal end of the treatment site. The first elongate delivery member of the distal instrument accessory device 201 may be coaxial with and/or may telescope within the second elongate delivery member of the proximal instrument accessory device

203. The stylets may be removed, and inflation fluid 150 may be supplied into the elongate delivery members of the distal and proximal instrument accessory devices 201, 203 to inflate the expandable members 230 on either end of the treatment site 100. A catheter may be passed over the guidewire and through an instrument lumen of the proximal accessory device to a position between the expandable members. Treatment fluid delivered through the catheter may be contained within the treatment site 100 between the expandable members.

In various embodiments, an elongate delivery member may be a flexible member, which may comprise rubber, silicone, polymer, metal, alloy, liquid silicone rubber, natural rubber, or the like. More rigid materials, such as polymers and metal, may be selected to provide structure and support compared to less rigid materials, such as silicone, which may be selected to provide sealing between and/or against the expandable member. The elongate delivery member may be solid or comprise a lumen, such as an inflation lumen. The elongate delivery member may be in fluid communication with the expandable member. The elongate delivery member may be disposed between the proximal end of the expandable member and the distal end of the expandable member. The inflation lumen may be welded, soldered, brazed, bonded, glued, adhered, or otherwise fixedly attached to the body.

In various embodiments, an expandable member may have an expanded configuration and an unexpanded configuration. An expandable member may comprise a variety of compliant, semi-compliant, or non-compliant materials. These materials may comprise silicone, latex, polyurethane, rubber, isobutylene or the like. The thickness of a wall of the expandable member may vary with the material and may relate to the outer diameter of the expandable member in the unexpanded and the expanded configuration. An expandable member may be expanded and unexpanded or otherwise stretched once or a plurality of times to increase its elasticity prior to use within a patient, which may improve a symmetrical inflation of the expandable member and may improve the centering mechanics of the expandable member. An expandable member may be expanded via a supply of an inflation fluid through one or more inflation lumens via one or more elongate delivery members. The same inflation lumen may be used to expand and un-expand the expandable member. Alternatively, a supply inflation lumen and a return inflation lumen may be intermittently or continuously used to circulate inflation fluid through an expandable member. A continuous flow of inflation fluid through a supply inflation lumen and a return inflation lumen may substantially maintain a desired pressure of the inflation fluid within the expandable member, or the inflation fluid may be heated and circulated to maintain a desired temperature with the expandable member. A single elongate delivery member may include multiple lumens and/or a bifurcated lumen for inflation fluid.

In various embodiments, a treatment fluid supplied through a catheter may include embolization fluids (such as microspheres, occlusive beads, Y90 beads or the like), contrast, saline, a drug, blood, or the like.

In various embodiments, an inflation fluid supplied through an elongated delivery member may include saline, water, $CO_2$, dilute contrast media, or the like.

In various embodiments, a method of delivering a treatment fluid through a body lumen may include inserting a guidewire through an instrument lumen of a first catheter accessory. The guidewire is advanced, e.g., through an access sheath, through a body lumen to a first treatment site of a patient and a catheter is inserted into the instrument lumen about the guidewire. The catheter may be inserted over the guidewire into the body lumen through the access sheath. The catheter is advanced to the first treatment site. During insertion and advancement of the guidewire and/or catheter, the accessary device is maintained outside of the body. After the guidewire and/or catheter are at the treatment site, the first catheter accessory is advanced along the catheter to a point proximal to the first treatment site. The catheter accessory may be advanced with a stylet reversibly coupled to and extending through the inflation lumen. An inflation fluid may be inserted into the inflation lumen (after removal of the stylet, if used) to expand the expandable member, and a treatment fluid may be supplied through the catheter. The treatment fluid may comprise microspheres, occlusive beads, Y90 beads, or contrast dye. After delivery of the treatment fluid, the expandable member may be unexpanded, a stylet reinserted into the inflation lumen, and the first catheter accessory removed from the body or moved to a second treatment site. The stylet may then again be removed, and the expandable member re-expanded, and a second dose of treatment fluid supplied.

In various embodiments, a method of delivering a treatment fluid through a body lumen may also include inserting the guidewire through a second instrument lumen of a second catheter accessory. The expandable member expands when the inflation lumen is supplied with inflation fluid. This embodiment creates a first treatment site between the first expandable member and the second expandable member. For example, the guidewire may be extended through both instrument lumens and advanced through the patient's body. A catheter may be extended over the guidewire. One catheter accessory followed by the other catheter accessory may be moved sequentially or together into position over the catheter. If an expandable member other than an expandable balloon is used, the treatment fluid may be delivered in substantially the same way as described. To transition the expandable member(s) between the expanded and unexpanded configurations, a mechanism may be actuated (e.g., mechanically actuated, electrically actuated, pneumatically actuated) from the proximal end of the delivery member. A mechanism may extend from the proximal end in a distal direction along the delivery member to an expandable member, to transition the configuration of the expandable member.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:
1. An instrument accessory device, comprising:
a body having a proximal end, a distal end, a longitudinal axis, and a wall defining an instrument lumen extending between the proximal end and the distal end along the longitudinal axis of the body, the instrument lumen having an inlet and an outlet at the respective proximal end and distal end of the body, the instrument lumen configured to slidingly receive a length of an instrument extendible through the instrument lumen;
an expandable member disposed about the wall at the distal end of the body, the expandable member extending between a proximal end and a distal end along a longitudinal axis of the expandable member;
an elongate delivery member having a proximal end and a distal end that is attached to the body, the body positioned at the distal end of the elongate delivery member, the elongate delivery member comprising an inflation lumen extending between the proximal end of the elongate delivery member and the distal end of the elongate delivery member and in fluid communication with the expandable member at the distal end of the elongate delivery member;

a handle at the proximal end of the elongate delivery member, wherein the inflation lumen is continuous with a handle lumen extending along the handle; and a stylet removably receivable within the inflation lumen, the stylet having a cap at a proximal end of the stylet, the cap reversibly coupleable to the handle;

wherein the elongate delivery member is configured to slide the instrument lumen of the body and the expandable member along the length of the instrument when extended therethrough.

2. The device of claim 1, wherein the expandable member is adhered to the wall at the proximal and distal ends of the expandable member.

3. The device of claim 1, wherein the distal end of the elongate delivery member is disposed between the proximal end of the expandable member and the distal end of the expandable member.

4. The device of claim 1, wherein the instrument is a guidewire, a catheter, or the catheter combined with the guidewire.

5. The device of claim 1, wherein the expandable member is pneumatically, electrically, or mechanically expandable.

6. The device of claim 1, wherein the expandable member comprises a self-expanding or shape memory material.

7. The device of claim 1, wherein the inflation lumen is configured to communicate a fluid between the proximal end of the elongate delivery member and the expandable member.

8. The device of claim 1, wherein the distal end of the elongate delivery member and the proximal end of the expandable member are adhered to the wall at the proximal end of the body.

9. The device of claim 1, wherein the expandable member comprises a compliant balloon or semi-compliant balloon.

10. A catheter system, comprising:
an instrument; and
a catheter accessory slidably disposable about the instrument, comprising:
a body having a proximal end, a distal end, a longitudinal axis, and a wall defining an instrument lumen extending between the proximal end and the distal end along the longitudinal axis of the body, the instrument lumen having an inlet and an outlet at the respective proximal end and distal end of the body, the instrument lumen configured to slidingly receive a length of the instrument extendible through the instrument lumen;
an expandable balloon coupled to the body;
an elongate delivery member attached at a distal end of the elongate delivery member to the body and having an inflation lumen extending therethrough in fluid communication with the expandable balloon, the body positioned at the distal end of the elongate delivery member;
a handle at a proximal end of the elongate delivery member, wherein the inflation lumen is continuous with a handle lumen extending along the handle; and
a stylet removably receivable within the inflation lumen, the stylet having a cap at a proximal end of the stylet, the cap reversibly coupled to the handle;
wherein the elongate delivery member is configured to slide the instrument lumen of the body and the expandable member along the length of the instrument when extended therethrough.

11. The system of claim 10, wherein the instrument comprises a guidewire, a catheter, or the catheter combined with the guidewire.

12. The system of claim 10, wherein the instrument comprises a guidewire, a catheter, or the catheter disposable about the guidewire.

13. The system of claim 10, wherein the expandable balloon comprises a compliant balloon or semi-compliant balloon.

14. A method of delivering a treatment fluid within a patient using the catheter system of claim 10, the method comprising:
inserting the instrument through the instrument lumen of the catheter accessory, wherein the instrument is a guidewire;
advancing the guidewire through a body lumen to a first treatment site within the patient;
inserting a catheter into the instrument lumen about the guidewire;
advancing the catheter to the first treatment site;
advancing the catheter accessory along the catheter to a position proximal to the first treatment site;
expanding the expandable balloon about the catheter accessory to occlude the body lumen at the proximal position; and
supplying a treatment fluid through the catheter to the first treatment site.

15. The method of claim 14, wherein expanding comprises supplying a fluid through the inflation lumen to inflate the expandable balloon.

16. The method of claim 14, further comprising:
deflating the expandable balloon;
moving the catheter to a second treatment site;
moving the catheter accessory to a position proximal to the second treatment site;
re-inflating the expandable balloon; and
supplying the treatment fluid through the catheter to the second treatment site.

* * * * *